(12) United States Patent
Vo et al.

(10) Patent No.: US 7,399,291 B2
(45) Date of Patent: Jul. 15, 2008

(54) CATHETER FOR TREATMENT OF TOTAL OCCLUSIONS AND METHODS FOR MANUFACTURE AND USE OF THE CATHETER

(75) Inventors: Minh Vo, Sugar Hill, GA (US); Cory Anderson, Alpharetta, GA (US)

(73) Assignee: Syntheon, LLC., Miami, FL (US)

( * ) Notice: Subject to any disclaimer, the term of this patent is extended or adjusted under 35 U.S.C. 154(b) by 0 days.

(21) Appl. No.: 11/291,758

(22) Filed: Dec. 1, 2005

(65) Prior Publication Data

US 2006/0264821 A1    Nov. 23, 2006

Related U.S. Application Data

(60) Provisional application No. 60/633,145, filed on Dec. 2, 2004.

(51) Int. Cl.
*A61F 7/12* (2006.01)
*A61F 7/00* (2006.01)
*A61M 29/00* (2006.01)

(52) U.S. Cl. ............... 604/96.01; 604/113; 607/104

(58) Field of Classification Search ......... 604/95.05, 604/96.01, 113, 95.01, 103; 606/170, 171, 606/180, 167, 192–196; 600/585; 607/104, 607/113, 114
See application file for complete search history.

(56) References Cited

U.S. PATENT DOCUMENTS

| | | | |
|---|---|---|---|
| 5,041,089 A * | 8/1991 | Mueller et al. | 604/103.09 |
| 5,506,300 A | 4/1996 | Ward et al. | |
| 5,814,705 A | 9/1998 | Ward et al. | |
| 5,895,718 A | 4/1999 | Ishimura et al. | |
| 6,126,684 A * | 10/2000 | Gobin et al. | 607/113 |
| 6,160,084 A | 12/2000 | Langer et al. | |
| 6,270,522 B1 | 8/2001 | Simhambhatla et al. | |
| 6,336,936 B2 | 1/2002 | Simhambhatla et al. | |
| 6,342,047 B1 | 1/2002 | Urakawa et al. | |
| 6,388,043 B1 | 5/2002 | Langer et al. | |
| 6,491,672 B2 * | 12/2002 | Slepian et al. | 604/267 |
| 6,532,720 B2 | 3/2003 | Anderson | |
| 6,550,480 B2 | 4/2003 | Feldman et al. | |
| 6,583,194 B2 | 6/2003 | Sendijarevic | |
| 6,680,359 B2 | 1/2004 | Schoenheider | |
| 6,720,402 B2 | 4/2004 | Langer et al. | |
| 6,759,481 B2 | 7/2004 | Tong | |

(Continued)

*Primary Examiner*—Matthew F Desanto
(74) *Attorney, Agent, or Firm*—Mayback & Hoffman, P.A.; Gregory L. Mayback; Scott D. Smiley

(57) ABSTRACT

A catheter for treatment of chronic total occlusions includes an occlusion breach device, a catheter body made of a temperature-dependent softening, shape-memory, thermoplastic polymer having a first flexible state and a second stiff state. The catheter body has a heat transfer conduit and a conduit for slidably receiving the breach device. A heat-transferring device selectively changes a temperature of the heat transfer conduit to, thereby, change stiffness of the catheter body between the two states. To treat a CTO with the catheter, it is warmed above the glass-transition temperature and below the melting-temperature to make the catheter flexible. The catheter has a shape when inserted at the occlusion site and is cooled to, thereby, stiffen. Breaching of the occlusion is assisted with the stiff catheter. The catheter is removed by warming the polymer. Also provided is a method for manufacturing such a selectively stiffening catheter.

2 Claims, 14 Drawing Sheets

U.S. PATENT DOCUMENTS 6,800,085 B2 10/2004 Selmon et al.
6,827,325 B2 12/2004 Hofmann et al.
7,066,931 B2 6/2006 O'Connor et al.
2005/0273145 A1* 12/2005 Saab .......................... 607/113

* cited by examiner

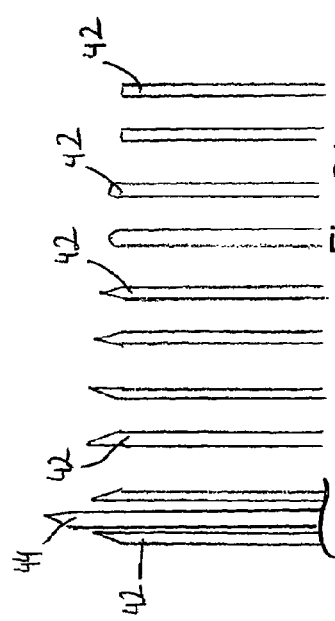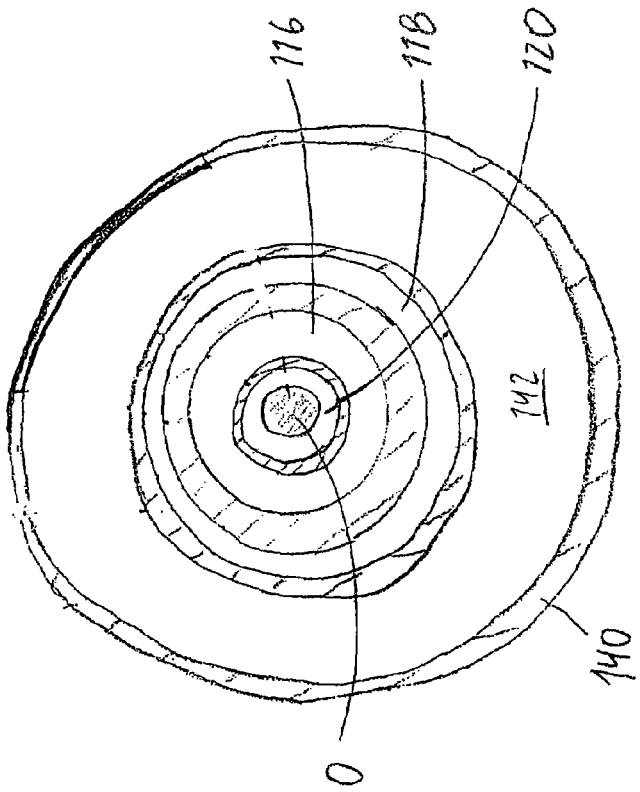

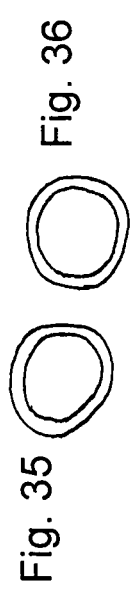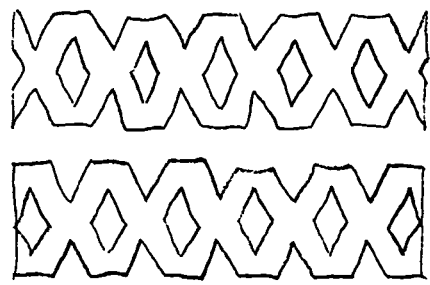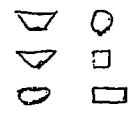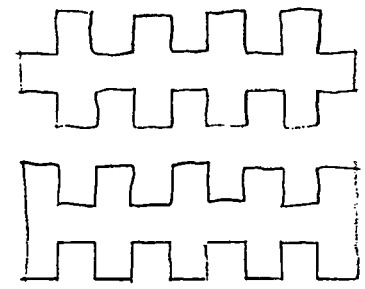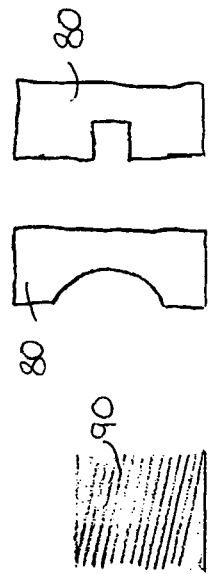

CATHETER FOR TREATMENT OF TOTAL OCCLUSIONS AND METHODS FOR MANUFACTURE AND USE OF THE CATHETER

CROSS-REFERENCE TO RELATED APPLICATION

This application claims the benefit under 35 U.S.C. § 119 (e) of U.S. Provisional Applications No. 60/633,145, filed Dec. 2, 2004, and entitled "Catheter for Treatment of Total Occlusions," the complete disclosure of which is hereby incorporated by reference herein in its entirety.

BACKGROUND OF THE INVENTION

1. Field of the Invention

The present invention relates to a catheter, especially a catheter for treatment of acute, sub-acute, or chronic total occlusions ("CTOs"), in particular, the catheter facilitates crossing CTOs of the coronary or peripheral vasculature, and methods for manufacture and use of the catheter.

2. Description of Related Prior Art

Catheters for treating chronic total occlusions exist in the prior art. For example, U.S. Pat. No. 6,800,085 to Selmon et al. (hereinafter "Selmon") describes a catheter system for treatment of occluded blood vessels.

The prior art catheters, however, are not able to circumnavigate vasculature in a flexible state and, when ready to treat a vessel occlusion, to become fixed in the vasculature so that virtually all of the force acting upon the occlusion is used against the occlusion instead of on the catheter to displace the catheter proximally. Accordingly, it would be beneficial to provide a catheter that has the ability to change its flexibility state from flexible and soft to hard and rigid upon the command of the user.

SUMMARY OF THE INVENTION

It is accordingly an object of the present invention to provide a catheter for treatment of chronic total occlusions, in particular, a catheter that facilitates crossing CTOs of the coronary or peripheral vasculature, and methods for manufacture and use of the catheter that overcome the hereinaforementioned disadvantages of the heretofore-known devices and methods of this general type and that is able to change its flexibility state from flexible and soft to hard and rigid upon the command of the user and, thereby, permits an improved crossing of CTOs of the coronary or peripheral vasculature.

The device takes advantage of the properties of commercially available softenable, shape-memory, thermoplastic polymers, hereinafter referred to as the "polymer." The polymer is a polyurethane base and is a thermoplastic able to be softened. The polymer has a broad and relatively flat melt temperature-to-glass transition temperature (hereinafter "MTGT temperature") that provides unique shape memory characteristics—characteristics taken advantage of by the present invention. One example of the polymer is a product sold by The Polymer Technology Group, Inc., under the name Calo•MER™ and can be presently found on the Internet at www.polymertech.com. Specifically with regard to the present invention, the polymer allows the manufacture of a catheter that has a controlled flexible-to-stiff shape memory property.

If the polymer is heated to a temperature above its glass transition temperature, but below its melting temperature, the internal stress in the polymer is released and the polymer softens and becomes flexible. When the temperature is dropped below the glass transition temperature, the internal stresses return to the polymer, and it stiffens in its then-existing shape.

The polymer can be either heat-set or cold-formed into a specifically defined shape. The heat-set process can be explained by the following steps:

extruding the polymer in the desired shape, for example, a tube;

softening the tube by warming it above its glass-transition temperature;

shaping the tube into a desired shape by constraining it in a mold, for example;

heating the tube in the constrained shape in an oven at approximately 110° C. for approximately 20 minutes; and removing the tube from the oven, removing the tube from the constraint, and cooling the tube to room temperature to heat-set the shape into the polymer.

When the polymer so formed is warmed above its glass-transition temperature, but below its melting-temperature, it becomes flexible and can be moved into various desired shapes. If the polymer is, then, cooled below its glass-transition temperature, it hardens and assumes the shape it was in when cooled. If the polymer is, again, warmed above its glass-transition temperature but below its melting-temperature, it returns to its heat-set shape.

The polymer can be cold-formed into a specific shape through injection molding. The polymer is melted and injection molded into the desired shape and, then, when it is cooled, it retains the desired specific shape.

During manufacture of the polymer, additives can be mixed into the polymer to permit a shift of the glass-transition-temperature and the melting-temperature. Thus, the MTGT temperature can be selected according to the particular desired use (or to a particular patient). Additives may also be included in the polymer during manufacture to create radio opacity or to enhance the strength of the polymer.

The polymer is well suited for medical devices because it is biocompatible, extrudable, and injection moldable. For medical applications, human body temperature may be used to effect this change in the polymer. For example, the glass-transition temperature and the melting-temperature may be selected so that, when the polymer is placed inside the body and warms to body temperature, the polymer will either harden or soften as described above.

There are three potential significant conditions of interest for medical applications:

the polymer may have a glass-transition temperature and melting-temperature such that it is soft at body temperature;

the polymer may have a glass-transition temperature and melting-temperature such that it is hard at body temperature; and the polymer may have a glass-transition temperature and/or a melting-temperature such that it transitions between the hard and soft conditions at body temperature.

One exemplary use for the polymer when formed into a vascular catheter is to engage and/or treat a total occlusion ("CTO"). Engaging a CTO is made possible by positioning a guidewire or other puncturing device at a first surface of the CTO facing the catheter and using this puncturing device to penetrate entirely through the CTO. As can be expected, pressure upon the CTO by a device controlled at the proximal end of the catheter, but located at the distal end of the catheter, causes proximal displacement of the distal end away from the CTO. This is not the case for the catheter of the present invention.

The catheter is moved in the vasculature to the CTO in its flexible state. When in a position for treating the CTO, the catheter is cooled to transition the polymer of the catheter into its rigid state. When in the rigid state, the curves of the catheter "hug" the tortuous path of the vasculature and form holding surfaces that substantially prevent longitudinal movement of catheter. This rigid catheter, therefore, is able to counteract pressure exerted in the proximal direction caused by moving the puncturing device into the CTO. Accordingly, for such circumstances, the variable flexibility of the catheter provides a rigid platform to prevent the catheter from exiting the artery ostium and to provide better torque and force transmission from the cardiologist's hands to the distal tip of the catheter.

In summary, the flexible-to-stiff transition ability of the polymer provides a platform for a catheter that is flexible enough to navigate through tortuous anatomy when flexible, but, once the catheter navigates through the anatomy and is in a position for treatment, it may be frozen in place to, thereby, provide a rigid platform for receiving the guidewire or other device that will be used to engage a total occlusion or other difficult lesion.

When in place in the vessel, the portion of the catheter near the CTO will have relatively the same shape as the vessel in which the CTO is present. This orientation permits the puncturing device to be place somewhere closer to the center of the CTO than to the edge thereof. Clinically, engaging the center of the CTO is better than engaging a side thereof, in particular, a side of the CTO that contacts and is-attached to the vessel wall. This is especially true because removal of the CTO near the vessel wall can cause the vessel to tear or cause the penetrating device to puncture the vessel on the other side of the CTO—both of these conditions are potentially fatal to the patient. Where the CTO is located in a curved vessel, puncturing the CTO virtually guarantees puncture of the vessel wall as the plane of the CTO varies from being orthogonal to the longitudinal extent of the puncturing device toward a direction parallel to the longitudinal extent. Accordingly, to enhance CTO treatment, the present invention can include a balloon located at the distal tip for centering the catheter in the vessel and for ensuring that the inner puncturing member engages the CTO at a center point with respect to the vessel. To further decrease the slippage possibility, the balloon may have a slightly abrasive, uneven, or non-slip surface that prevents the catheter from moving away from the CTO when the puncturing member/guidewire is advanced.

It is noted that various features of the catheter of the present invention are independent from the features relating to the polymer. In an embodiment of the catheter not containing the polymer, the catheter body can be made of other plastics such as pebax, polyimide, polyethylene, or nylon. In such a case, the heat transferring fluid (hot or cold) and the send and return lumens for transporting the fluid are rendered unnecessary. For example, the coaxial embodiments or the multi-lumen embodiments could be constructed out of these materials and use a balloon for centering the catheter and/or use the CTO-puncturing device for attacking the CTO, etc., and not require the stiffness transition properties.

With the foregoing and other objects in view, there is provided, in accordance with the invention, a catheter for treatment of chronic total occlusions, including an occlusion breaching device, a catheter body of a temperature-dependent softening, shape-memory, thermoplastic polymer having a first relatively flexible state and a second relatively stiff state, the catheter body having a heat transfer conduit and an occlusion device conduit for slidably receiving the occlusion breaching device therein, and a heat-transferring device fluidically connected to the heat transfer conduit and selectively changing a temperature of the heat transfer conduit to, thereby, change a stiffness of the catheter body from the first flexible state to the second stiff state.

In accordance with another feature of the invention, the occlusion breaching device includes a guidewire, a mandrel having a tip, a hypo tube, or a variable stiffness guidewire having an outer flexible sheath and a movable mandrel inside the outer flexible sheath. The occlusion breaching device has a cannula and a puncture slidably disposed in the cannula for piercing a chronic total occlusion. The occlusion breaching device is formed to cross a chronic total occlusion of a coronary vessel or a peripheral vessel.

In accordance with a further feature of the invention, occlusion breaching device has a longitudinal axis and a removable rotating device selectively rotates the occlusion breaching device about the axis. The rotating device selectively rotates the occlusion breaching device between approximately 100 and 1,000 RPM. The rotating device can be an electric motor.

In accordance with an added feature of the invention, the catheter body has a distal end and the occlusion breaching device has a vacuum fluidically connected to the distal end for drawing matter from the occlusion site through the catheter body.

In accordance with an additional feature of the invention, the polymer has a melt temperature-to-glass transition temperature of approximately body temperature. The polymer can have a melt temperature-to-glass transition temperature between approximately 35° C. and 39° C., between approximately 15° C. and 35° C., or between approximately 39° C. and 59° C.

In accordance with yet another feature of the invention, the polymer is relatively soft and flexible when at a temperature above the glass transition temperature and below the melting temperature and is relatively stiff when at a temperature below the glass transition temperature.

In accordance with yet a further feature of the invention, the polymer is relatively stiff when at a temperature above the glass transition temperature and below the melting temperature and is relatively soft and flexible when at a temperature below the glass transition temperature.

In accordance with yet an added feature of the invention, the polymer includes additives shifting the glass-transition-temperature and the melting-temperature of the polymer up or down.

In accordance with yet an additional feature of the invention, the polymer can have a glass-transition temperature and melting-temperature causing the catheter body to be soft at approximately body temperature or the polymer can have a glass-transition temperature and melting-temperature causing the catheter body to be hard at approximately body temperature, or the polymer has a glass-transition temperature and/or a melting-temperature causing the catheter body to be between the first flexible state and the second stiff state approximately at body temperature.

In accordance with again another feature of the invention, the heat transfer conduit has a send conduit supplying a heating medium to the distal end of the catheter body for supplying heat thereto and a return conduit for removing the heating medium from the distal end.

In accordance with again a further feature of the invention, the heat transfer conduit has a fluid send lumen, a fluid return lumen, and a connection area fluidically connecting the fluid send lumen and the fluid return lumen at the distal end of the catheter body.

In accordance with again an added feature of the invention, the heat transfer conduit has a fluid send lumen and a fluid return lumen fluidically connected to the fluid send lumen at intervals in the catheter body.

In accordance with again an additional feature of the invention, the catheter body has a distal portion of the polymer and a proximal portion of a material different from the polymer.

In accordance with still another feature of the invention, there is provided a centering device connected to the catheter body and centering the catheter body in a vessel in which the catheter body is placed. The centering device can be a balloon that centers the catheter body in the vessel when inflated. The balloon can be disposed adjacent the distal end, preferably, within 3 cm of the distal end and surrounding the catheter body in a coaxial manner.

With the objects of the invention in view, there is also provided a method for manufacturing a selectively stiffening catheter for treatment of chronic total occlusions, including the steps of providing a temperature-dependent softening, shape-memory, thermoplastic polymer having a glass-transition temperature and a melting temperature, extruding the polymer in a tubular shape, warming the tube of the extruded polymer above the glass-transition temperature to soften the tube, constraining the tube in a mold to place the tube in a given shape, heating the constrained tube in at approximately 110° C. for approximately 20 minutes, and un-constraining and cooling the tube to room temperature to heat-set the given shape into the polymer.

With the objects of the invention in view, there is also provided a method for treating a chronic total occlusion, including the steps of warming the catheter of the instant invention above the glass-transition temperature and below the melting-temperature to make the catheter relatively flexible, inserting the flexible catheter in a patient to an occlusion site, the catheter having a given shape when at the occlusion site, cooling the catheter below the glass-transition temperature to make the catheter relatively stiff and, thereby, have the catheter assume the given shape, breaching the occlusion to be treated with the occlusion breaching device, warming the polymer above the glass-transition temperature and below the melting-temperature to make the catheter relatively flexible and removing the catheter from the patient.

In accordance with still a further mode of the invention, pressure exerted by breaching of the occlusion is counteracted with the catheter stiffened in the given shape.

In accordance with still an added mode of the invention, before carrying out the breaching step, the catheter is centered at the occlusion site, preferably, by providing a balloon approximately at a distal end of the catheter and inflating the balloon when the catheter is at the occlusion site.

In accordance with a concomitant mode of the invention, the breaching step is carried out by providing a sharp piercing device centered in the catheter and extending the piercing device when the distal end of the catheter is adjacent the occlusion site.

Other features that are considered as characteristic for the invention are set forth in the appended claims.

Although the invention is illustrated and described herein as embodied in a catheter for treatment of chronic total occlusions and methods for manufacture and use of the catheter, it is, nevertheless, not intended to be limited to the details shown because various modifications and structural changes may be made therein without departing from the spirit of the invention and within the scope and range of equivalents of the claims.

The construction and method of operation of the invention, however, together with additional objects and advantages thereof, will be best understood from the following description of specific embodiments when read in connection with the accompanying drawings.

BRIEF DESCRIPTION OF THE DRAWINGS

FIG. 13 is a cross-sectional view of the catheter of FIGS. 11 and 12;

FIG. 14 is a fragmentary, cross-sectional view of a portion of a first exemplary profile of the balloon of FIG. 12;

FIG. 15 is a fragmentary, cross-sectional view of a portion of a second exemplary profile of the balloon of FIG. 12;

FIG. 16 is a fragmentary, cross-sectional view of a portion of a third exemplary profile of the balloon of FIG. 12;

FIG. 17 is a fragmentary, cross-sectional view of a portion of a fourth exemplary profile of the balloon of FIG. 12;

FIG. 18 is a fragmentary, cross-sectional view of a distal portion of a first embodiment of a cannula of the catheter of FIGS. 11 and 12;

FIG. 19 is a fragmentary, cross-sectional view of a distal portion of a second embodiment of a cannula of the catheter of FIGS. 11 and 12;

FIG. 20 is a fragmentary, cross-sectional view of a distal portion of a third embodiment of a cannula of the catheter of FIGS. 11 and 12;

FIG. 21 is a fragmentary, cross-sectional view of a distal portion of a fourth embodiment of a cannula of the catheter of FIGS. 11 and 12;

FIG. 22 is a fragmentary, cross-sectional view of a distal portion of a fifth embodiment of a cannula of the catheter of FIGS. 11 and 12;

FIG. 25 is a side elevational view of a first embodiment of a radiopaque marker according to the invention;

FIG. 26 is a plan view of the marker of FIG. 25;

FIG. 27 is a side elevational view of a second embodiment of a radiopaque marker according to the invention;

FIG. 28 is a plan view of the marker of FIG. 27;

FIG. 29 is a fragmentary, side elevational view of a shapable wire or ribbon for the catheter according to the invention;

FIG. 30 is an enlarged cross-sectional view of the wire or ribbon of FIG. 29;

FIG. 31 is a side elevational view of a first patterned inner member according to the invention;

FIG. 32 is a side elevational view of the inner member of FIG. 31 rotated 90°;

FIG. 33 is a side elevational view of a second patterned inner member according to the invention;

FIG. 34 is a side elevational view of the inner member of FIG. 33 rotated 90°;

FIG. 35 is a plan view of the inner member of FIGS. 31 and 33; and

FIG. 36 is a plan view of the inner member of FIGS. 32 and 34.

DETAILED DESCRIPTION OF THE PREFERRED EMBODIMENTS

Figure 1:
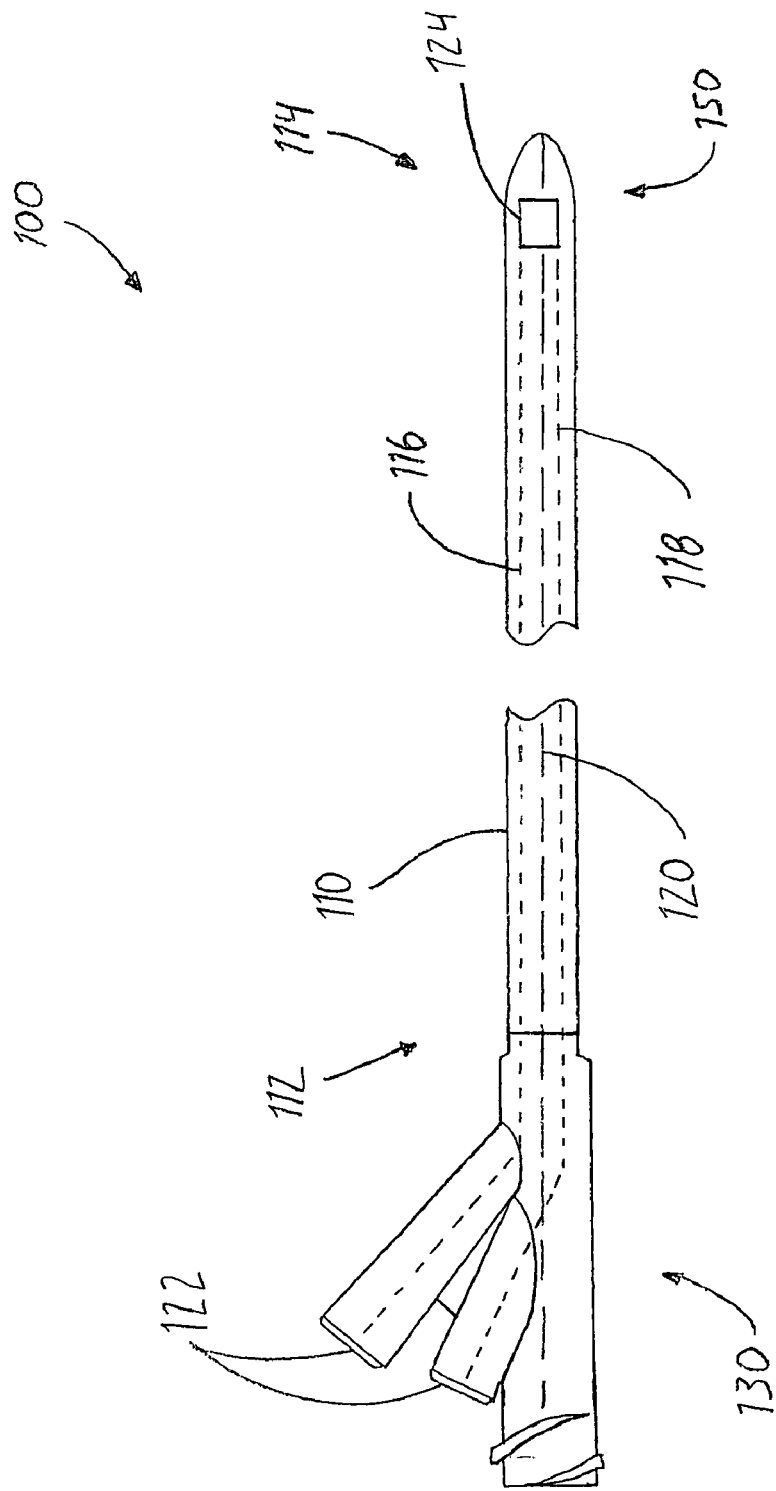
FIG. 1 is a fragmentary, side elevational and partially hidden view of a first embodiment of a catheter according to the invention.

While the specification concludes with claims defining the features of the invention that are regarded as novel, it is believed that the invention will be better understood from a consideration of the following description in conjunction with the drawing figures, in which like reference numerals are carried forward.

Before the present invention is disclosed and described, it is to be understood that the terminology used herein is for the purpose of describing particular embodiments only and is not intended to be limiting. It must be noted that, as used in the specification and the appended claims, the singular forms "a," "an," and "the" include plural references unless the context clearly dictates otherwise.

Referring now to the figures of the drawings in detail and first, particularly to FIG. 1 thereof, there is shown a general diagrammatic embodiment of a variably flexible catheter 100 according to the invention. The catheter 100 has a catheter body 110 having a proximal end 112 and a distal end 114. A proximal connection assembly 130 is disposed at the proximal end 112. In the embodiments shown in FIGS. 1 to 3, the proximal connection assembly 130 is trifurcated. A distal occlusion treatment assembly 150 is disposed at the distal end 114.

Figure 2:
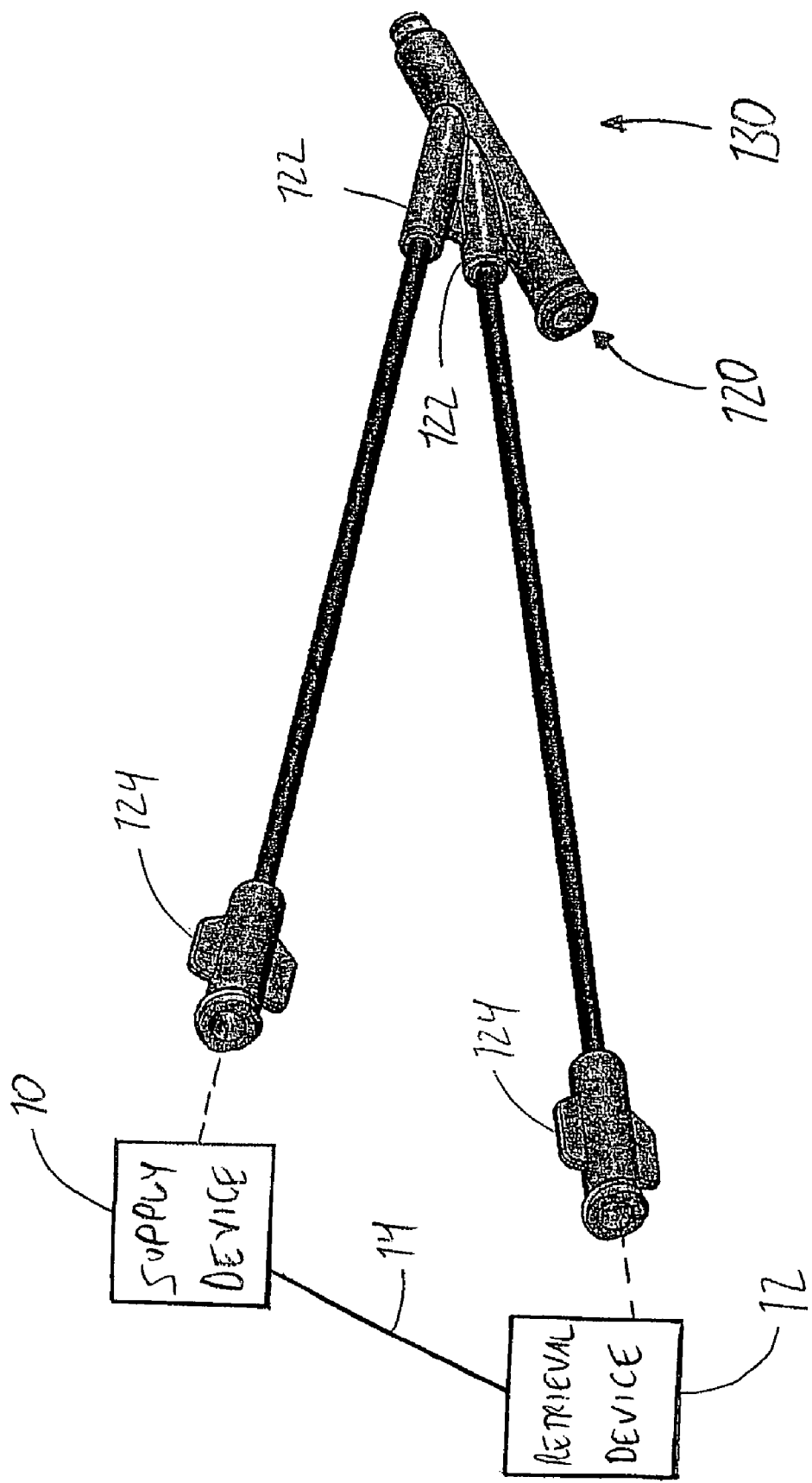
FIG. 2 is a perspective view of a proximal connector of the catheter of FIG. 1 connected to a diagrammatic representation of a supply and return configuration.
Figure 3:
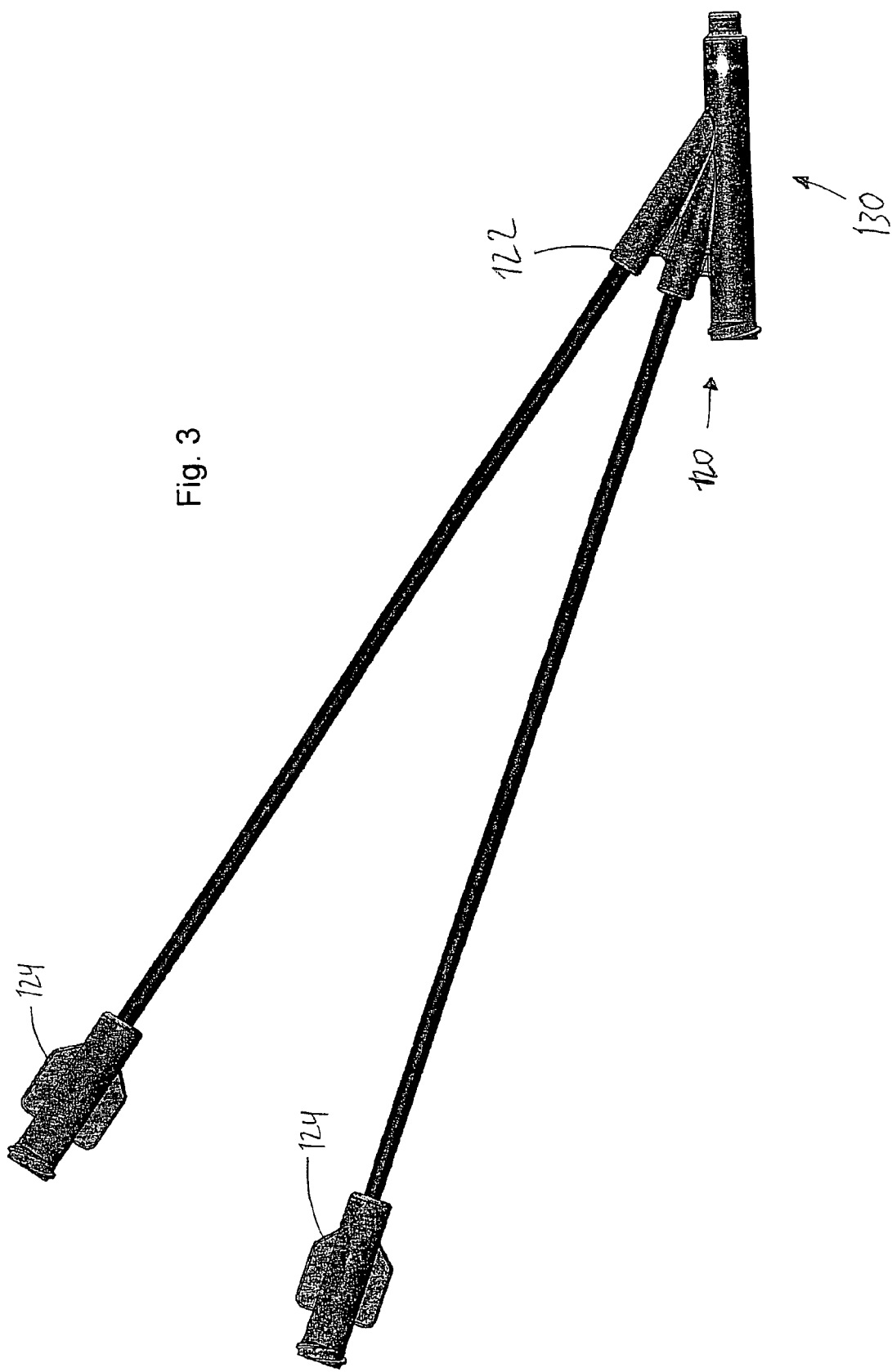
FIG. 3 is a side elevational view of the proximal connector of the catheter of FIG. 1.

The catheter body 110 defines a fluid send lumen 116, a fluid return lumen 118, and an operating lumen 120 for conveying a CTO puncturing device. The CTO puncturing device may be a standard guidewire, a mandrel with a blunt, hemispherical, or pointed tip, a hypo tube, or a variable stiffness guidewire with a movable mandrel inside an outer flexible sheath. At the proximal end 112 of the catheter body 110, the fluid send lumen 116 and the fluid return lumen 118 are separate and are each provided with a respective fluid input/output connector 122. Each of the fluid connectors 122 has, for example as shown in FIGS. 2 and 3, a female end 124 of a luer connector that is shaped to connect to a supply device 10 for supplying a fluid and to a retrieval device 12 for receiving the supplied fluid after it has traversed through the catheter 100 and has transferred heat thereto (heating or cooling). A line 14 can connect the supply device 10 to the retrieval device 12 for completing a fluid circuit if the fluid is to be circulated into and out from the fluid send lumen 116 and the fluid return lumen 118 in a continuous manner. Alternatively, the supply device 10 and the retrieval device 12 can be in one unit or integral. The fluid need not be a liquid; it can also be a gas, if desired.

One simple example of the supply device 10 can include a syringe for supplying the fluid send lumen 116 with a fluid. Similarly, a simple retrieval device 12 can be, for example, a container for retrieving the fluid supplied through the fluid send lumen 116. In another embodiment, an integral supply/retrieval system can include a reservoir for holding the heat transfer fluid, a heating and/or cooling device for transferring heat into or out from the fluid, and a pump for pumping the fluid through the send lumen 116 and, ultimately, to the reservoir from the return lumen 118.

Figure 4:
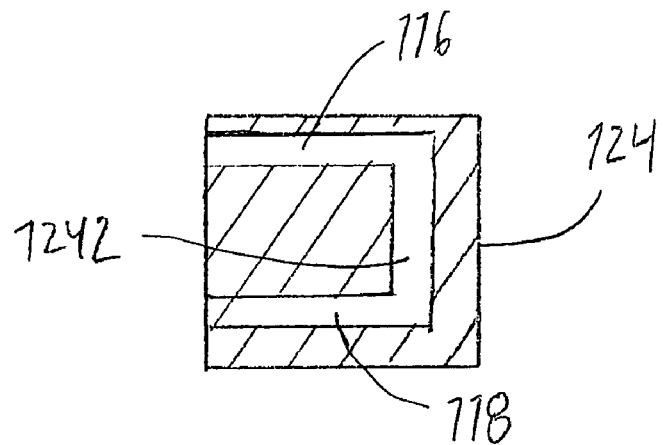
FIG. 4 is an enlarged, diagrammatic, cross-sectional view of a first embodiment of a connection area in the catheter of FIG. 1.
Figure 5:
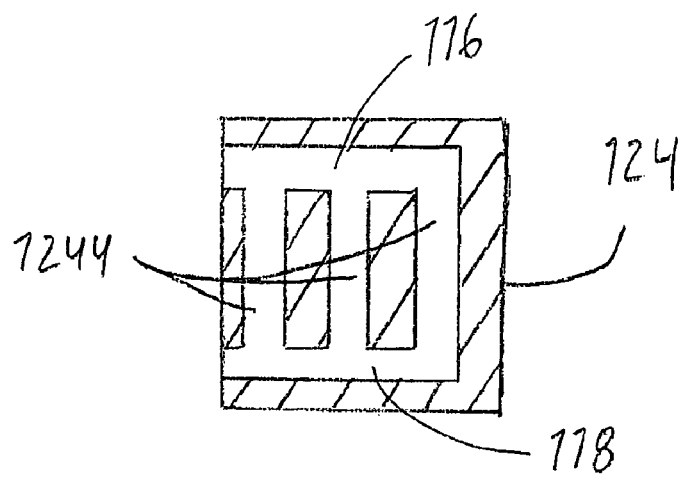
FIG. 5 is an enlarged, diagrammatic, cross-sectional view of a second embodiment of the connection area in the catheter of FIG. 1.
Figure 6:
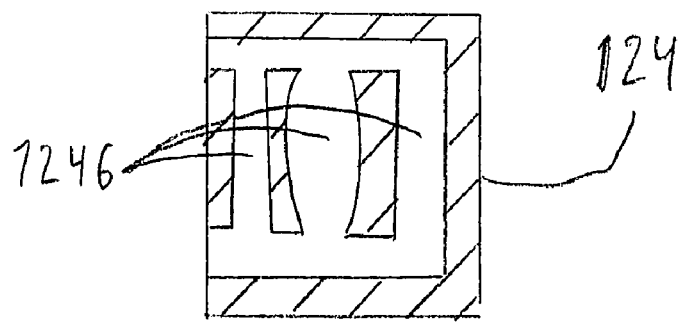
FIG. 6 is an enlarged, diagrammatic, cross-sectional view of a third embodiment of the connection area in the catheter of FIG. 1.

The fluid send lumen 116 and the fluid return lumen 118 are connected fluidically at the distal end 114 of the catheter body 110 at a connection area 124. This connection area 124 can take many forms. Thus, it is shown only diagrammatically in FIG. 1. A first example of the connection area 24 is shown in FIG. 4 and is formed by a bore 1242 fluidically connecting the fluid send lumen 116 and the fluid return lumen 118 to one another. A second example is shown in FIG. 5 and is formed by a plurality of bores 1244. A third example is shown in FIG. 6 and is formed by a plurality of differently shaped bores 1246. Any combination of connections in the connection area 124 is possible. What is necessary for the connection area 124 is only that the two lumens 116, 118 are fluidically connected to one another so that the fluid entering the fluid send lumen 116 can circulate through the catheter body 110 and exit the catheter body 110 through the fluid return lumen 118 (or vice-versa) such that the temperature of the catheter body 110 can be altered, whether evenly and asymmetrical, or unevenly and asymmetrically, or any other combination that is desired.

Figure 7:
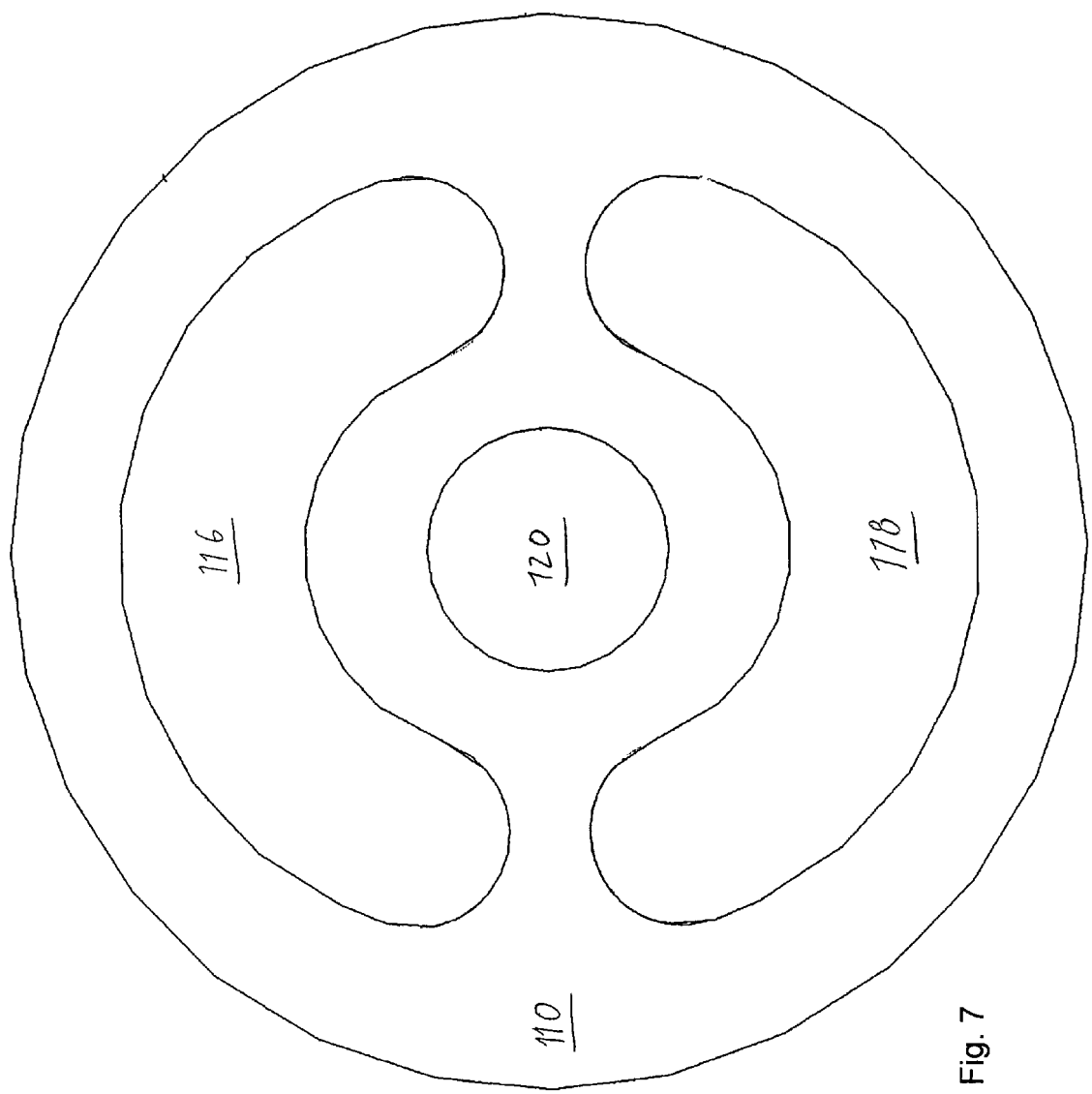
FIG. 7 is an enlarged, cross-sectional view of a first embodiment of a catheter body of the catheter of FIG. 1.
Figure 8:
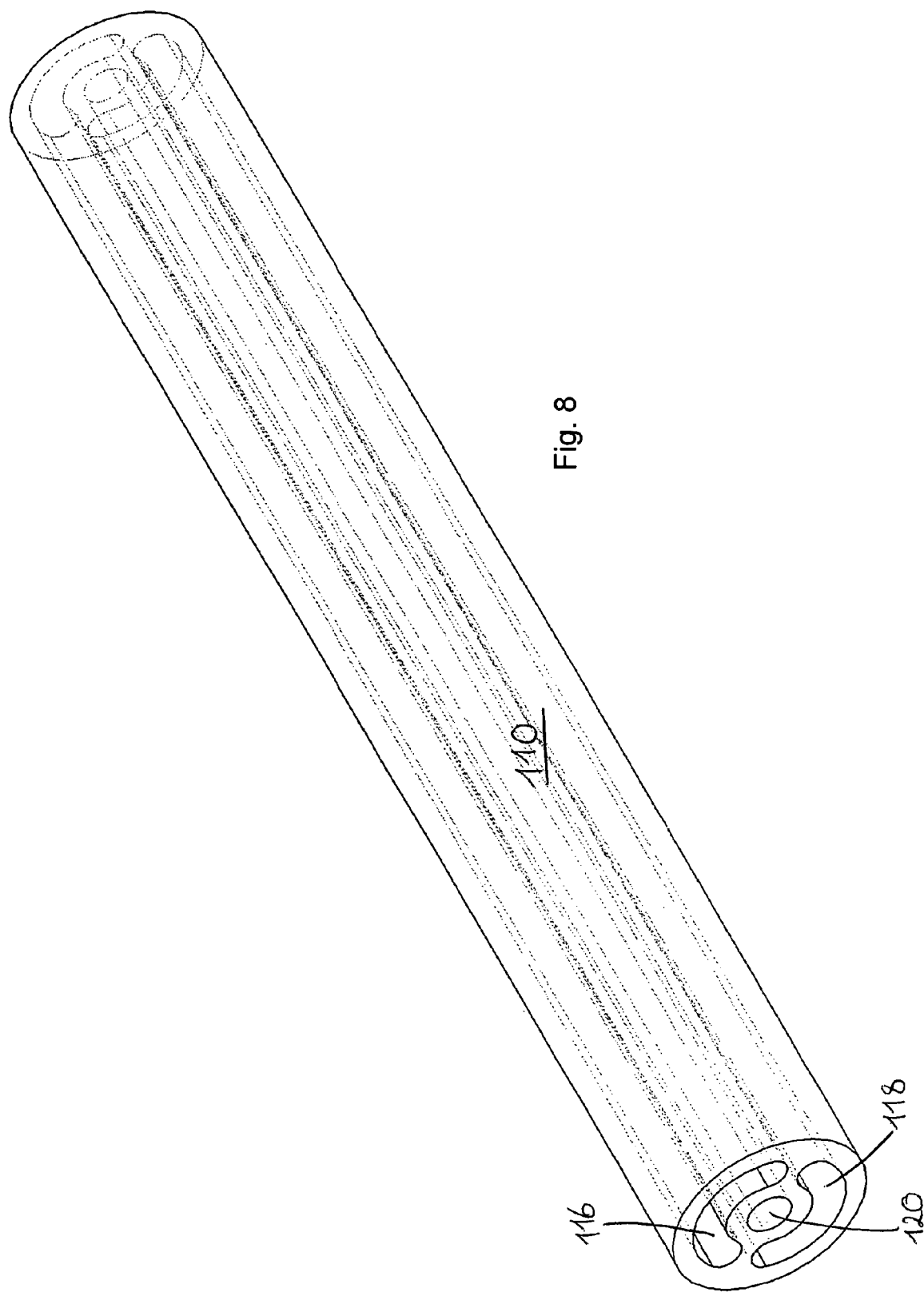
FIG. 8 is an enlarged, fragmentary, perspective view of the catheter body of FIG. 7.

For a catheter body 110 having a substantially circular cross-section, as shown in FIGS. 7 and 8, the fluid send and return lumens 116, 118 can be symmetrical about a diameter of the cross-section. The operating lumen 120 is centered on the longitudinal axis of the catheter body 110 and is substantially circular. In the embodiment of FIGS. 7 and 8, the two lumens 116, 118 are symmetrically disposed about the operating lumen 120.

The catheter 100 has a minimum of 3 lumens, which terminate at the proximal end 112 of the catheter 100 in a trifurcation 130 having the connections 122 fluidically connected to each lumen 116, 118, 120. To cool the catheter body 110, a cooled fluid can be sent to the distal end 114 first through the fluid send lumen 116, then through the connection area 124, and, finally, back through and out the fluid return lumen 118.

In another variation of the catheter, the catheter is made from a four-lumen tube. The function of three of the lumens 116, 118, 120 is the same as the catheter described above. The fourth lumen 130 has various uses, including, but not limited to:

inflating a balloon positioned at the distal end of the catheter;
  housing a stiffening wire for providing additional columnar strength;

housing a shapeable wire for causing a deflection in the catheter tip;

housing a shape memory alloy wire (such as nitinol) for causing a deflection in the catheter tip; and/or housing a wire anchored at the distal tip and attached to a proximal lever constructed to deflect the distal tip by imposing a force on the wire. It is noted that a stiffening sheath would be needed in such a configuration.

The catheter also may contain a plurality of send/return fluid lumens 116, 118, and these lumens need not be symmetrical or equal in number. For example, one send lumen 116 can have a larger diameter and can be connected to two return lumens 118 each having a relatively smaller diameter, or vice-versa. Of course, any combination of sizes and shapes can be used to tailor the catheter body 110 for heat distribution efficiency, for rapid transmission of the fluid, for reducing or increasing pressure of the fluid, and/or for any other reason.

The catheter 100 may contain different mixtures of the polymer at different locations along its length. For example, the proximal two thirds of the catheter 100 may be manufactured from the polymer in a first configuration having a relatively higher glass-transition temperature and the distal third of the catheter may be manufactured from the polymer in a second configuration having a relatively lower glass-transition temperature. Alternatively, the proximal portion of the catheter 100 may be manufactured from a completely different polymer than the polymer of the distal portion.

Figure 9:
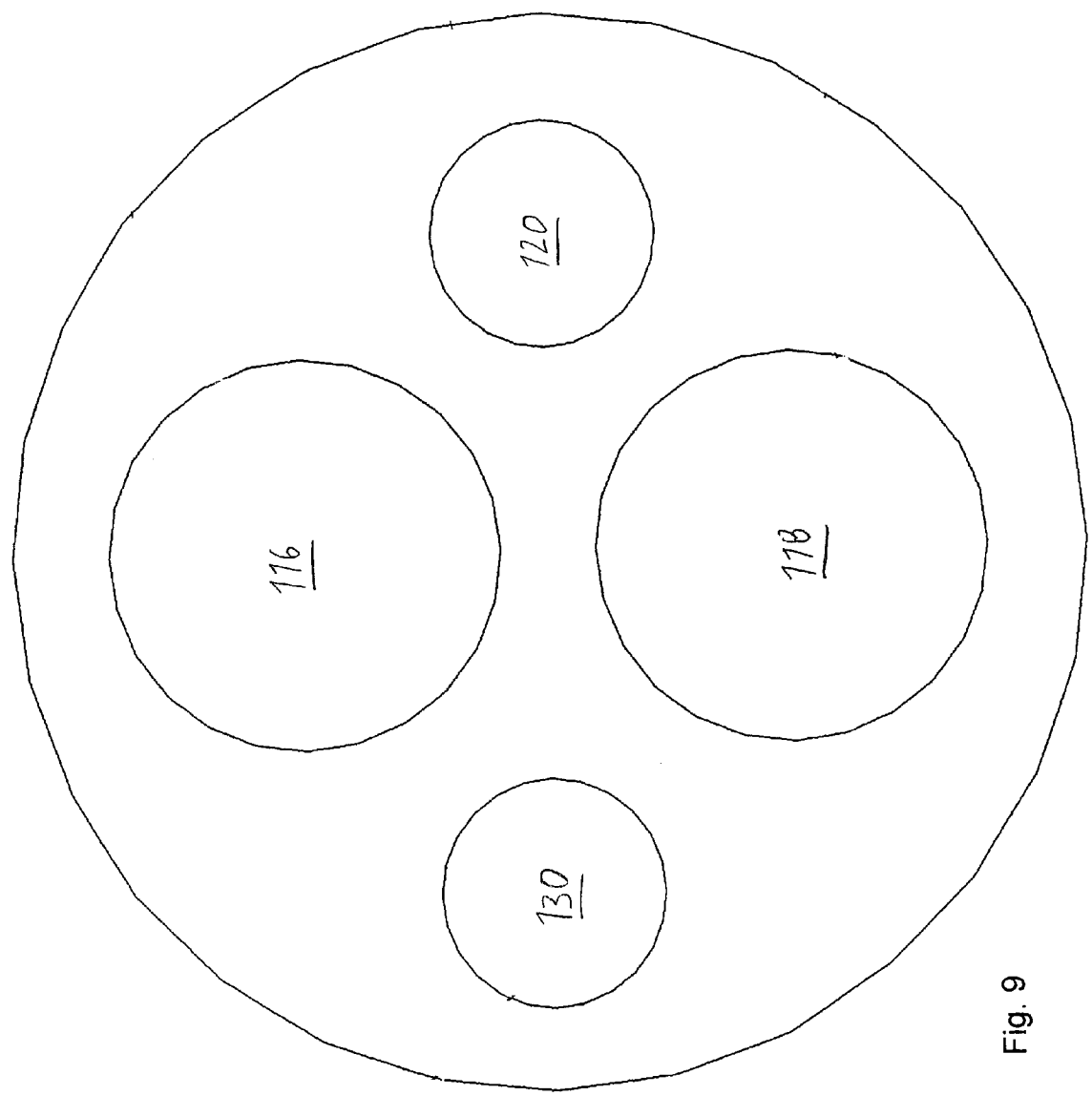
FIG. 9 is an enlarged, cross-sectional view of a second embodiment of a catheter body of the catheter of FIG. 1.
Figure 10:
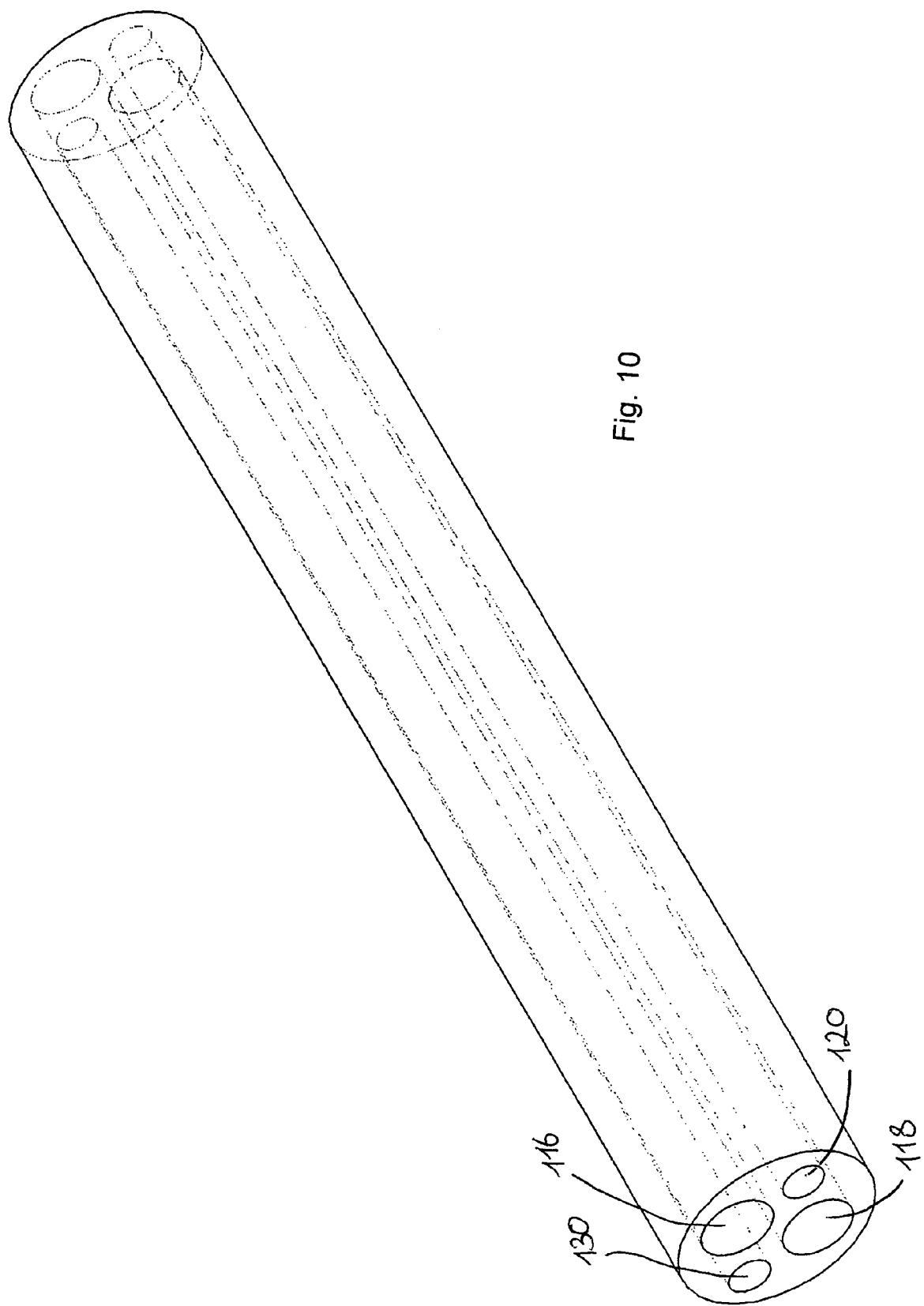
FIG. 10 is an enlarged, fragmentary, perspective view of the catheter body of FIG. 9.

The catheter body 110 need not be limited to three lumens. As shown in FIGS. 9 and 10, the fluid send and return lumens 116, 118 can be symmetrical about a first diameter of the cross-section. The operating lumen 120 and a secondary lumen 130 can be also symmetrical about a second diameter of the cross-section that is orthogonal to the first diameter. In this embodiment, all four lumens 116, 118, 120, 130 are substantially circular, but need not be.

As described above, CTOs are best treated when the catheter body 110 is disposed centrally in the vessel containing the CTO. To center the catheter body 110 in the vessel to be treated, a balloon 140 is disposed at or near the distal end 114 of the catheter 100. Preferably, the balloon 140 is 1 mm to 5 mm long and is disposed within 3 cm of the distal-most end of the catheter 100. The balloon may be constructed from a compliant or semi-compliant polymer allowing a single catheter to serve a variety of vascular diameters.

Figure 11:
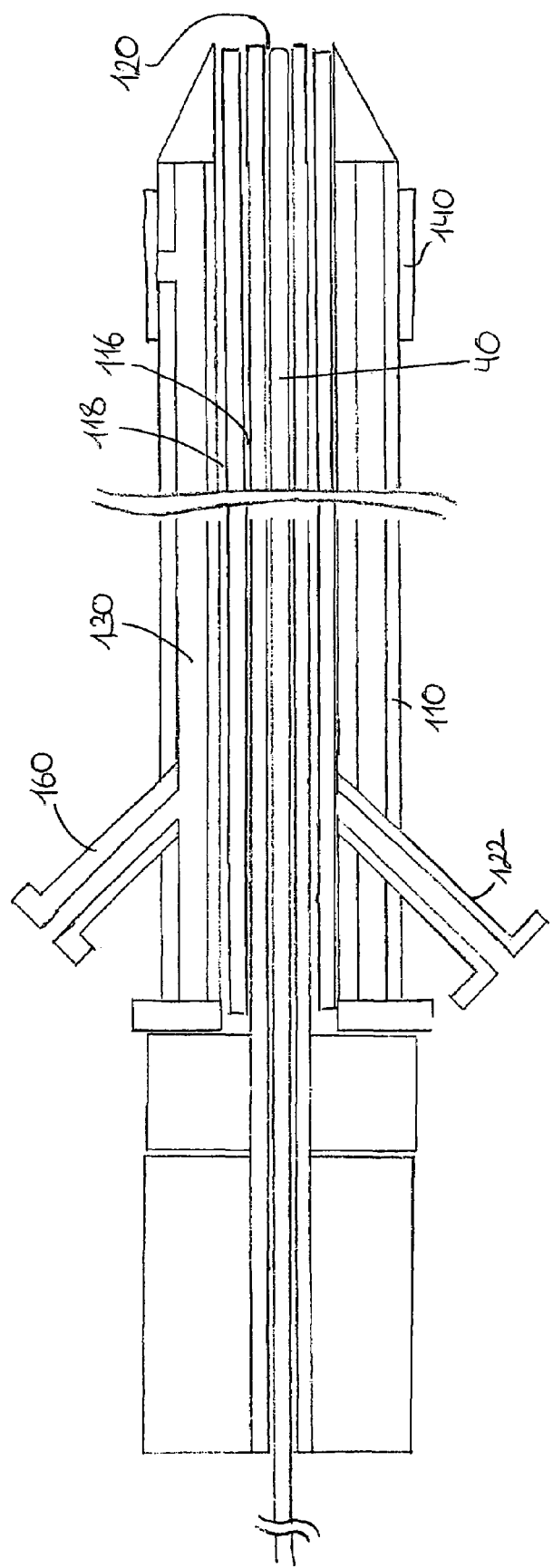
FIG. 11 is a fragmentary, cross-sectional view of a second embodiment of a catheter with balloon according to the invention with the balloon in a deflated state.
Figure 12:
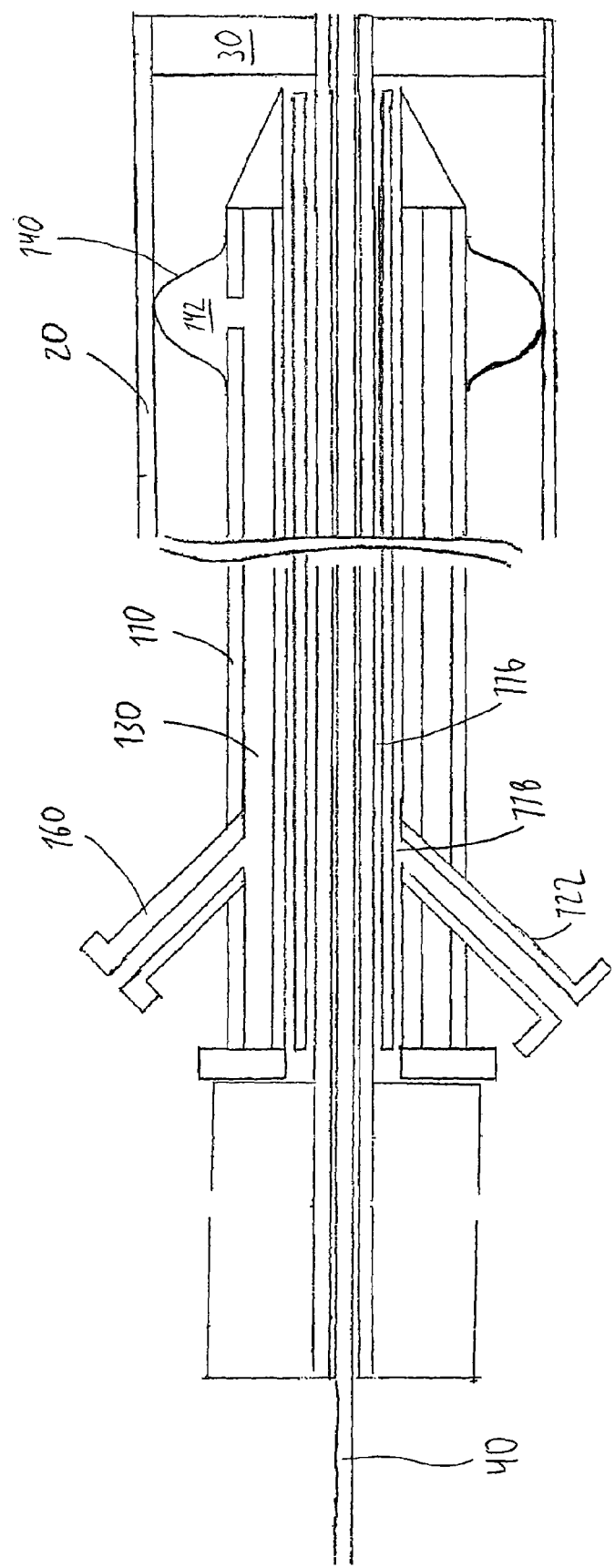
FIG. 12 is a fragmentary, cross-sectional view of the catheter of FIG. 11 with the balloon in an inflated state in a vessel next to a CTO and with a cannula and puncture passing through the CTO.

Even though the coaxial configuration is shown in FIGS. 11 to 13, it is noted that the four-lumen configuration illustrated in FIGS. 7 to 10 can be used as well.

To describe the centering movement provided by the balloon 140 on the catheter body 110, reference is made to FIGS. 11 to 17. The secondary lumen 130 in this embodiment is a balloon inflation lumen 130. An interior 142 of the balloon 140 is fluidically connected to the inflation lumen 130. The balloon 140 is inflated through a connector 160 disposed at the proximal end of the inflation lumen 130. See FIGS. 11 and 12. Typically, a female end of a luer connector forms the connector 160 and is shaped to connect to a non-illustrated inflation device, for example, a distal end of a syringe for inflation of the balloon 140.

In the embodiment shown in FIGS. 11 to 13, the lumens 116, 118, 120 and the balloon 140 are coaxial. As the distal end 114 traverses the vasculature 20 towards the CTO 30, the balloon 140 is in its deflated, folded state (see FIG. 11). When the distal end 114 is within approximately 5 cm of the CTO 30, the balloon 140 is inflated (see FIG. 12). Because the balloon 140 is disposed symmetrically about the inner member housing the puncturing device 40, when the balloon 140 is inflated, the puncturing device 40 is centered in the vessel 30 as clearly shown in FIG. 12. In this position, the puncturing device 40 may be used to break through the CTO as shown in FIG. 12.

The balloon 140 need not be curved or somewhat circular (see FIG. 16). It can have various profiles including trapezoidal (see FIG. 14), pyramidical (FIG. 15), and triangular (FIG. 17).

The puncturing device 40 can be made in two parts, a cannula 42 and a puncture 44 centrally disposed in the cannula 42. The distal end of the cannula 42 can have various shapes including tapered inward (FIG. 18), tapered outward (FIG. 19), pointed (FIG. 20), rounded (FIG. 21), and squared (FIG. 22). The same is true for the shape of the puncture 44.

There are three possible configurations for the setting the glass transition temperature and melting temperature with respect to body temperature (which is defined herein as being within a range of approximately 35° C. to approximately 39° C.): soft at body temperature, hard at body temperature, and in transition at body temperature. It is assumed, in the following description of the various possibilities of MTGT temperature, that the catheter is manufactured from the polymer and that the catheter is constructed for vascular applications.

Under the first possibility for MTGT temperature, the polymer has a MTGT temperature below body temperature.

When the catheter is introduced into the body, it will be warmed to approximately 37° C. Warming the polymer will soften it and make it flexible by releasing its internal stress (as described above). If the catheter was heat-set or cold-formed during the manufacturing process, and if it was unconstrained by a sheath (such as a guiding catheter), it would assume the heat-set/cold-formed shape inside the body. The catheter may be constructed to allow the polymer to be cooled below its glass-transition temperature. Introducing a chilled fluid into the catheter and circulating the fluid through the catheter could achieve this cooling. When the catheter is cooled, it will harden in its then-existing shape. This phenomenon would be temporary because the cooling source could be removed and, then, the catheter would gradually return to body temperature and soften again. There are several key advantages of this approach when using such a polymer for the catheter of the present invention:

- When the catheter is inside the patient, it is in a fail-safe configuration because it is in its soft (flexible) condition. Therefore, if there is any failure of the cooling source, the catheter can be safely removed because it is soft and flexible, or will be as soon as the body warms it up.
- Chilled saline is available as the cooling agent. If, for some reason, the integrity of the catheter were compromised in the patient, leakage of the cooled saline would have little or no negative physiological effect on the patient.
- Circulating cooled fluid in the catheter does not introduce any electricity or other energy source into the patient.
- The stiffness of the catheter is proportional to the cooling fluid's temperature and/or flow rate. Therefore, a specific stiffness in the catheter could be achieved by delivering a carefully regulated temperature and flow rate of the cooled fluid.

Under the second possibility for MTGT temperature, the polymer has a MTGT temperature above body temperature.

If the polymer has a MTGT temperature above body temperature, when the catheter is introduced into the body, it will be warmed to approximately 37° C. At 37° C., the catheter is rigid. However, if the catheter is warmed above body temperature and above its glass-transition temperature, it softens. Such warming above body temperature can be achieved by inductive heating. For example, the tip of the catheter could contain a non-illustrated heater element that is electrically insulated from the patient. With respect to FIG. 9, for example, the fourth lumen 130 or another fifth lumen could contain therein the heater element. Electrical current could be introduced to the heater element. In such an embodiment, energy, in the form of heat, will be emitted as the electrical current passes through the resistive wire. The heat warms the polymer above body temperature and above the glass-transition temperature, making the polymer soft. When the electrical current is removed, the catheter cools to body temperature and stiffens.

Under the third possibility for MTGT temperature, the polymer has a MTGT temperature at or near body temperature.

When such a catheter is introduced into the body, it will be warmed to approximately 37° C. At 37° C., the catheter is in a transition state between soft and rigid. While the same methods for either cooling or warming the catheter (as describe above) could be used, there may be clinical advantages to have the polymer be in the transition state when it is at 37° C. One significant advantage is that the polymer could provide the necessary support from its semi-rigid state with enough navigability from its semi-softened state so that no outside energy is necessary.

Figure 23:
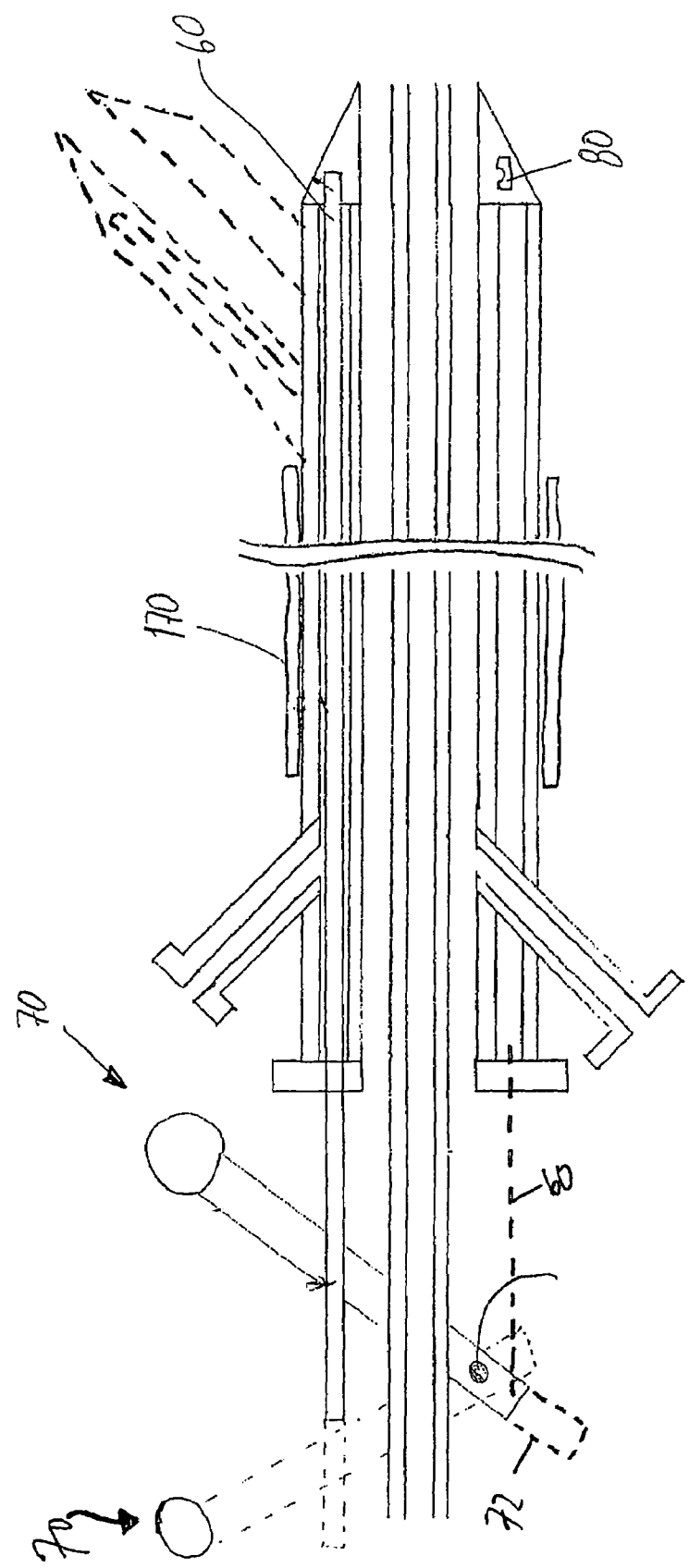
FIG. 23 is a fragmentary, cross-sectional view of another embodiment of the catheter according to the invention with a lever-induced deflection.
Figure 24:
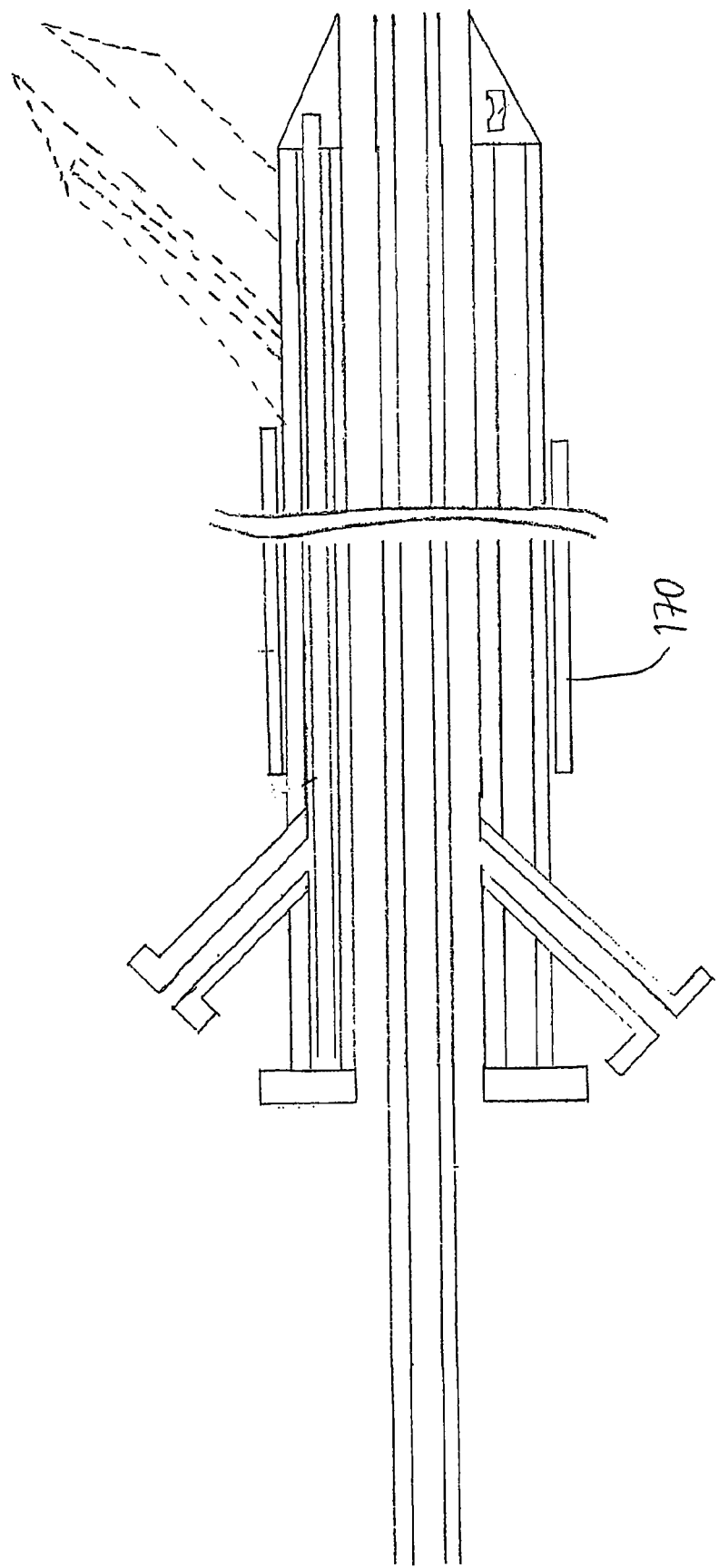
FIG. 24 is a fragmentary, cross-sectional view of still another embodiment of the catheter according to the invention with a shape-memory-induced deflection.

Optionally, an outer member 170 (see FIG. 23) could be added to the catheter 100 on the outside thereof. The outer member 170 can provide one or all of the following attributes:
improved torquability;
improved column strength; and/or
thermal insulation.

Several variations of the invention are described below, along with specific advantages of the configuration.

The balloon 140 at the distal tip 114 centers the catheter body 110 in the vessel, thus, ensuring that the inner member engages the CTO at its center. Additionally, the balloon 140 may have a slightly abrasive or non-slip surface that prevents the catheter body 110 from slipping proximally away from the CTO when the inner member and/or guidewire are advanced. The inner member (depending upon the embodiment, for example, FIGS. 18 to 22) is either configured (1) to puncture the tough fibrous cap of the occlusion, (2) to burrow through the occlusion as the inner member is rotated at a given speed, preferably between approximately 100 RPM and 1,000 RPM, or (3) to prevent the deflection of a guidewire toward the vessel wall as a guidewire is advanced to engage the occlusion. The luminal space between the outer member and middle member that is pressurized to inflate the balloon is also configured to provide additional guidewire support. Finally, it is noted that, when a pressurized fluid is introduced into the intraluminal space of the catheter body 110, the catheter body 110 stiffens to provide additional guidewire support.

One puncturing device 40 of present invention is a tube (having a polymer or metal composition) and a cannula mounted to a distal end thereof. The cannula is made from a hard metal, such as titanium, titanium alloy, stainless steel alloy, engineering plastics, or medical ceramics. The cannula is sharpened with a very thin or tapered tip (similar to a drill bit used for drilling holes in catheters). The inner member and distal cannula have an inner diameter sufficient to allow a standard diameter guidewire to freely pass through them (0.014", 0.018", or 0.035"). All or part of the cannula and/or inner member may be made from polymers that are radiopaque or they may be coated with radiopaque polymers.

A puncturing device system can include an electric motor fixedly connected to the inner member at a proximal end of the inner member to spin the inner member between approximately 100 RPM and 1000 RPM, as the interventional cardiologist manually advances the catheter through the CTO. Alternatively, a device for manually spinning the inner member (e.g., a crank and gear assembly) can be provided to contact the proximal end of the inner member as the interventional cardiologist manually advances the catheter through the CTO. The manual-spinning device for rotating the inner member is, preferably, a removable attachment constructed to grip the proximal end portion of the inner member. The attachment may be configured to engage the guidewire exit port of the trifurcation and to also lock the inner member in an axial position and/or a radial position. Additionally, the attachment may engage a guidewire-torqueing device that, itself, grips the guidewire.

A vacuum can also be connected on the proximal end of the inner member and, thereby, be connected fluidically to the CTO disposed inside and/or near the inner member. In such a configuration, the vacuum can aspirate particulate at the CTO and free the distal cannula to advance through the CTO.

Additionally, and/or alternatively, the catheter system described above can include a system 70 for deflecting the tip of the catheter 100. Deflection of the catheter tip is achieved by anchoring the tip of a wire 60 in the distal tip 114 of the catheter 100 (see FIG. 23). A proximal end of the wire 60 is connected to a lever 70, which is housed inside a handle. To move the wire 60 (and, thereby, deflect the distal tip 114), an operator manually actuates the lever 70 and causes the wire 60 to move proximally. A setscrew or ratchet system can be incorporated into the lever to ensure that deflection of the wire 60 is maintained. In such an embodiment, the outer member 170 of the catheter is a stiff sheath along the entire length except for the distal segment, which is configured to deflect. Because the wire 60 is fixed at the distal tip, the proximal deflection of the wire 60 causes the tip of the catheter to deflect as shown, for example, in FIG. 23. The desired angle of deflection can be between 0° and approximately 90°. A second pull wire 60 (dashed line in FIG. 23) could be incorporated to allow deflection in a direction opposite the deflection direction of the first pull wire 60. Such a wire 60 could be connected to the lever 70 at a distal part 72.

A radiopaque component 80 can be added at or near the tip to provide an indicator signaling the deflection and/or the orientation of the catheter tip 114 to the operator. For example, the radiopaque component 80 could be rectangular in shape with an arc portion removed from one side thereof that corresponds to the orientation of the arc that will be created when the catheter is deflected. Alternative configurations of the opaque component 80 are shown in FIGS. 25 to 28.

The system can also have a device for shaping the inner member or that includes a shapeable wire or ribbon 90 in the intraluminal space between the outer member and the middle member. In such an embodiment, the balloon 140 would not be required because the cardiologist can "aim" the catheter tip 114 in the desired direction using the shaping device. The radiopaque component 80 is added at or near the tip 114 to provide a visual indicator to the operator regarding the orientation of the catheter. For example, the radiopaque component 80 could be rectangular in shape with an arc of polymer removed from one side that corresponds to the orientation of the arc that will be created when the catheter is deflected. See FIGS. 25 to 28.

The inner member can be made out of a shape memory alloy or can include a wire or ribbon manufactured out of a shape memory alloy in the intraluminal space between the outer member and the middle member, the wire or ribbon taking shape at body temperature. The desired shape is an angle of deflection between 0° and 90°. The tip of the inner member's cannula can be radiopaque, so that the orientation of the shape memory alloy is visible under fluoroscopy. If a radiopaque component 80 is added at or near the tip 114, it will provide a visual indicator to the operator regarding the orientation of the catheter. For example, the radiopaque component 80 could be rectangular in shape with an arc of polymer removed from one side that corresponds to the orientation of the arc that will be created when the catheter is deflected.

The inner member can also be manufactured out of a shape memory alloy, such as super-elastic nitinol.

In an alternative or additional embodiment, the proximal end of such an inner member can be subjected to a secondary process such as laser cutting to produce a specific pattern thereat. The pattern will maintain torquability of the inner member while also increasing the flexibility of the tube. For example, a spiral cut or other pattern, as shown in FIGS. 29 to 36, are exemplary possibilities. The distal end of such an inner member will contain the cannula described above. The cannula may be shaped from the existing superelastic nitinol inner member or may be welded onto the distal end of the inner member, for example.

Alternatively, and/or additionally, the inner member cannula is provided with a specially constructed distal tip formed out of a shape-memory alloy such as nitinol or a polymer. The distal tip is shaped similar to a pin vice. However, each of the pin vice "leaflets" is, in this embodiment, machined down to a needle-sharp point. At room temperature, the nitinol is in the closed, sharp position. At body temperature, the nitinol opens the "leaflets" into its spread shape. Additionally, the catheter has a balloon on the distal portion, similar to the balloon 140 described above.

A procedure for using the catheter device of the present invention involves positioning the sheathed sharp distal tip just proximal to the CTO. Next, the operator inflates the balloon to center the device in the vessel. Then, the sharp distal tip is advanced out of the catheter and into the CTO. Once the sharp tip has been positioned inside the CTO, the outer sheath will be withdrawn and the leaflets will expand outward, thus, separating the portion of the polymer contained in the proximal cap of the CTO. Finally, a standard guidewire is advanced through the separated CTO for further procedures to be undertaken.

As described above, the cannula or wire can be advanced with a ratchet device. This ratchet device can be similar to the mechanism for advancing the lead in a mechanical pencil. Such a mechanism provides precise control for advancing the wire and also provides grip for controlling (torque and linear advancement) of the guidewire or cannula.

We claim:

1. A catheter for treatment of chronic total occlusions, comprising:
    an occlusion breaching device having:
        a cannula; and
        a puncture slidably disposed in said cannula for piercing a chronic total occlusion;
    a catheter body of a temperature-dependent softening, shape-memory, thermoplastic polymer having a first relatively flexible state and a second relatively stiff state, said catheter body having:
        a distal end;
        a heat transfer conduit having:
            a send conduit supplying a heating medium to said distal end for supplying heat thereto; and
            a return conduit fluidically connected to said send conduit for removing the heating medium from said distal end; and
        an occlusion device conduit for slidably receiving said occlusion breaching device therein;
    a heat-transferring device fluidically connected to said heat transfer conduit and selectively changing a temperature of said heat transfer conduit to, thereby, change a stiffness of said catheter body from said first flexible state to said second stiff state;
    a centering device connected to said catheter body and centering said catheter body in a vessel in which said catheter body is placed; and
    a vacuum fluidically connected to said distal end of said catheter body for drawing matter at said distal end through said catheter body.

2. A method for treating chronic total occlusions, comprising:
    providing an occlusion breaching device with a cannula and a puncture slidably disposed in the cannula;
    providing a catheter body of a temperature-dependent softening, shape-memory, thermoplastic polymer having a relatively flexible state and a relatively stiff state with:
        an occlusion device conduit for slidably receiving the occlusion breaching device therein; and
        a heat transfer conduit, the heat transfer conduit having:
            a send conduit supplying a heating medium to the distal end for supplying heat thereto; and
            a return conduit fluidically connected to the send conduit for removing the heating medium from the distal end;
    traversing the catheter body up to a chronic total occlusion while in the flexible state to place the distal end adjacent the chronic total occlusion;
    traversing the occlusion breaching device through the occlusion device conduit to place a distal end of the puncture adjacent the distal end of catheter body;
    centering the distal end of the catheter body in the vessel adjacent the chronic total occlusion;
    fluidically connecting a heat-transferring device to the heat transfer conduit and selectively changing a temperature of the heat transfer conduit to, thereby, change a stiffness of the catheter body from the flexible state to the stiff state; and
    extending the puncture out from the distal end of the catheter body through the chronic total occlusion to create a breach in the chronic total occlusion.

* * * * *